United States Patent [19]

Welle et al.

[11] 4,406,904

[45] Sep. 27, 1983

[54] METHOD OF INHIBITING LUTEINIZING HORMONE SECRETION WITH 6,7-BENZOMORPHAN DERIVATIVES

[75] Inventors: Hendricus B. A. Welle, Maarssen, Netherlands; Magda Marko, Binningen, Switzerland

[73] Assignee: ACF Chemiefarma NV, Maarssen, Netherlands

[21] Appl. No.: 283,084

[22] Filed: Jul. 13, 1981

Related U.S. Application Data

[63] Continuation-in-part of Ser. No. 198,513, Oct. 20, 1980, abandoned.

[30] Foreign Application Priority Data

Oct. 23, 1979 [NL] Netherlands .................. 7907800

[51] Int. Cl.³ ........................................ A61K 31/485
[52] U.S. Cl. ................................................. 424/260
[58] Field of Search .......................................... 424/260

[56] References Cited

U.S. PATENT DOCUMENTS 4,202,897  5/1980  Babington ................... 424/260

OTHER PUBLICATIONS

Takeda et al., J. of Medicinal Chem., vol. 13, No. 6, (1970), pp. 1223–1224.

Katz et al., J. of Medicinal Chem., vol. 20, No. 11, (1977), pp. 1413–1419.
Lien et al., Chem. Abst., vol. 92, (1980), p. 34370k.
Brown et al., Chem. Abst., vol. 90, (1979), p. 180,048m.

*Primary Examiner*—Sam Rosen
*Attorney, Agent, or Firm*—Gerald D. Sharkin; Robert S. Honor; Thomas O. McGovern

[57] ABSTRACT

6,7-Benzomorphan derivatives of formula I,

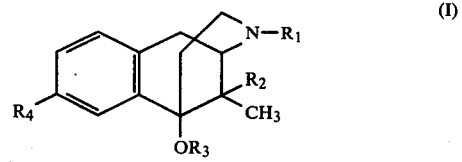

wherein $R_1$ is hydrogen; optionally hydroxy- and/or alkoxy-substituted alkyl, alkenyl, alkynyl, cycloalkyl or cycloalkylalkyl; alkenyloxyalkyl, aralkyl, arylhydroxyalkyl, aralkenyl or tetrahydrofurylalkyl; or optionally alkyl-substituted furylalkyl or isoxazolylalkyl, $R_2$ is hydrogen or methyl, $R_3$ is hydrogen, alkyl, alkenyl, alkynyl, aralkyl, hydroxyalkyl of alkoxyalkyl and $R_4$ is hydrogen, hydroxy, alkoxy or alkenyloxy, hydroxy groups in said compounds being each optionally acylated, having analgesic and luteinising hormone secretion inhibiting properties.

17 Claims, No Drawings

METHOD OF INHIBITING LUTEINIZING HORMONE SECRETION WITH 6,7-BENZOMORPHAN DERIVATIVES

The present application is a continuation-in-part of our previous application Ser. No. 198,513 filed Oct. 20, 1980, now abandoned.

The present invention relates to novel 6,7-benzomorphan derivatives.

The compounds 5-hydroxy- and 2',5-dihydroxy-2-methyl-6,7-benzomorphan as well as the 5-acetoxy- and 5-propionyloxy derivatives of the former and the 2',5-diacetoxy derivatives of the latter are known, e.g. from J. Med. Chem. 13, 1223 (1970) and J. Med. Chem. 20, 11, 1413–1419 (1977). Four of these compounds are said to possess weak analgesic activity of a lower order than that of the corresponding 5-H derivatives. The fifth compound is stated to possess no analgesic activity.

In accordance with the present invention it has now surprisingly been found that certain 5-oxy-substituted benzomorphans having a tertiary or quarternary carbon atom in the 9-position exhibit valuable pharmacological, in particular analgesic and narcotic-antagonist as well as luteinising hormone (LH) secretion inhibiting activity.

More particular the present invention provides compounds of formula I

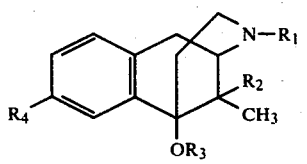

(I)

wherein
$R_1$ is hydrogen; optionally hydroxy- and/or alkoxy-substituted alkyl, alkenyl, alkynyl, cycloalkyl or cycloalkylalkyl; alkenyloxyalkyl, aralkyl, arylhydroxyalkyl, aralkenyl or tetrahydrofurylalkyl; or optionally alkyl-substituted furylalkyl or isoxazolylalkyl,
$R_2$ is hydrogen or methyl,
$R_3$ is hydrogen, alkyl, alkenyl, alkynyl, aralkyl, hydroxyalkyl or alkoxyalkyl and
$R_4$ is hydrogen, hydroxy, alkoxy or alkenyloxy,
whereby hydroxy groups in the compounds of formula I may each be optionally acylated.

In the above definition $R_1$ is preferably hydrogen; optionally hydroxy- and/or alkoxy-substituted alkyl, alkenyl, alkynyl or cycloalkylalkyl; aralkyl, arylhydroxyalkyl or tetrahydrofurylalkyl, or optionally alkyl-substituted furylalkyl. $R_3$ is preferably hydrogen, alkyl, alkenyl, hydroxyalkyl, aralkyl or alkoxyalkyl.

Saturated and unsaturated hydrocarbon chains in the compounds of formula I may be branched- or straight-chain and preferably contain maximally 6 carbon atoms. Multiple bonds are separated from the benzomorphan nucleus by at least two carbon atoms. Cycloalkyl groups and moieties preferably contain maximally 6 carbon atoms. Aryl is preferably phenyl.

Alkyl, alkenyl, alkynyl, cycloalkyl and cycloalkylalkyl groups as $R_1$ may be substituted, preferably mono- or di-substituted, more preferably mono-substituted, by hydroxy and/or alkoxy. Hydroxy and alkoxy substituents are separated from the benzomorphan nucleus by at least two carbon atoms. Acyl residues in $R_1$, $R_3$ and $R_4$ are preferably physiologically hydrolysable ester residues.

Aliphatic groups $R_1$ preferably contain maximally 6 carbon atoms in toto. Aliphatic groups $R_3$ and $R_4$ preferably contain 6 carbon atoms, more preferably 4 carbon atoms in toto. The aliphatic moieties of groups $R_1$ and $R_3$ having a terminal aryl, cycloalkyl or heterocyclic group preferably contain maximally 4, more preferably 2, carbon atoms. In $R_1$, when the terminal group is cycloalkyl or heterocyclic, the aliphatic moiety is most preferably methylene. Alkoxy substituents in a group $R_1$ preferably contain maximally 3, more preferably 2, carbon atoms, methoxy being the most preferred. Alkyl substituents on a furylalkyl or isoxazolyalkyl group $R_1$ are preferably methyl and such groups are preferably mono-substituted. As alkoxy substituents in a group $R_3$, methoxy and ethoxy, especially methoxy are preferred. Preferred acyl residues are phenylalkanoyl having maximally 4 carbon atoms in the alkanoyl moiety, alkanoyl having maximally 4 carbon atoms and nicotinoyl, especially benzoyl, acetyl and propionyl.

Preferred compounds of formula I are those wherein
$R_1$ is hydrogen, $C_{1-6}$ alkyl, $C_{1-6}$ hydroxyalkyl, $C_{2-6}$-(alkoxy-alkyl) in which the alkyl moiety is optionally mono-substituted by hydroxy or methoxy, $C_{3-6}$ alkenyl, $C_{3-6}$ alkynyl, $C_{4-7}$(cycloalkylmethyl), $C_{4-7}$[(1-hydroxycycloalkyl)-methyl], $C_{5-8}$[(1-methoxy-cycloalkyl)-methyl], $C_{7-10}$(phenylalkyl), $C_{7-10}$(phenylhydroxyalkyl), tetrahydrofurylmethyl or furylmethyl optionally ring-substituted by methyl,
$R_2$ is hydrogen or methyl,
$R_3$ is hydrogen, $C_{1-4}$ alkyl, $C_{1-4}$ hydroxyalkyl, $C_{3-4}$ alkenyl, $C_{3-4}$ alkynyl or $C_{7-9}$(phenylalkyl) and
$R_4$ is hydrogen, hydroxy, $C_{1-4}$ alkoxy or $C_{3-4}$ alkenyloxy,
whereby hydroxy groups in the compounds of formula I may each be optionally acylated.

In the compounds of formula I $R_1$ may be hydrogen. When it is alkyl it is preferably methyl, ethyl, n-propyl, n-butyl, iso-butyl, sek-butyl or n-hexyl, more preferably methyl, ethyl or n-butyl and most preferably methyl.

Hydroxy and alkoxy substituents in an aliphatic residue $R_1$ are preferably in the 2-position. Preferred alkoxy substituents are methoxy and ethoxy, methoxy being the most preferred. Hydroxy substituents as afforesaid may be acylated, preferred acyl groups being acetyl, propionyl and benzoyl, acetyl being the most preferred.

Preferred hydroxy- and/or alkoxy-substituted alkyl groups as $R_1$ are 2-hydroxypropyl, 2-hydroxybutyl, 2-hydroxy-2-methyl-propyl, 2-hydroxy-2-methylbutyl, 2-hydroxy-3-methoxypropyl, 2-methoxyethyl, 2-methoxypropyl, 2,3-dimethoxypropyl, 2-methoxybutyl, 2-methoxy-2-methylpropyl, 2-methoxy-2-methylbutyl, 2-ethoxyethyl and 2-isopropoxyethyl, especially 2-hydroxy-2-methylpropyl, 2-methoxyethyl, 2-methoxypropyl and 2-methoxy-2-methylpropyl, most especially 2-hydroxy- and 2-methoxy-2-methylpropyl. Preferred acyloxyalkyl groups as $R_1$ are 2-acetoxy- and 2-propionyloxy-2-methylpropyl the former being the most preferred.

When $R_1$ is alkenyl or alkynyl it is preferably allyl, 3-methyl-2-butenyl, propargyl or 3-butynyl, most preferably 3-butynyl. When $R_1$ is cycloalkylmethyl, it is preferably cyclopropylmethyl or cyclobutylmethyl.

$R_1$ may be e.g. (1-hydroxycycloalkyl)-methyl in which case the 1-hydroxy group may optionally be acylated, preferred acyl groups being acetyl, propionyl and benzoyl and in particular acetyl. As (1-hydroxycycloalkyl)-methyl $R_1$ is preferably (1-hydroxycyclopropyl)-, (1-hydroxycyclobutyl)- or (1-hydroxycyclopentyl)-methyl, most preferably (1-hydroxycyclopropyl)- or (1-hydroxycyclobutyl)-methyl. When $R_1$ is (1-acyloxycycloalkyl)-methyl this is preferably (1-acetoxycyclopropyl)-methyl, (1-acetoxy-cyclobutyl)-methyl or (1-acetoxy-cyclopentyl)-methyl, the first two of these being the most preferred.

When $R_1$ is (1-methoxycycloalkyl)-methyl, this is preferably (1-methoxycyclopropyl)-, (1-methoxycyclobutyl)- or (1-methoxycyclopentyl)-methyl, (1-methoxycyclopropyl)- and (1-methoxycyclobutyl)-methyl being most preferred.

When $R_1$ is phenylalkyl, this is preferably benzyl or phenethyl. When $R_1$ is phenylhydroxyalkyl this is preferably β-hydroxyphenethyl. When $R_1$ is tetrahydrofurylmethyl or furylmethyl optionally ring-substituted by methyl, this is preferably tetrahydrofurfuryl, furfuryl, 3-furylmethyl, 3-methylfurfuryl or 2-methyl-3-furylmethyl, more preferably tetrahydrofurfuryl, furfuryl and 3-methylfurfuryl and most preferably tetrahydrofurfuryl.

$R_2$ may be hydrogen or methyl. Preferably $R_2$ is methyl.

$R_3$ may be hydrogen. When $R_3$ is alkyl this is preferably methyl, ethyl, n-propyl or n-butyl, more preferably methyl or ethyl. When $R_3$ is hydroxyalkyl this is preferably 3-hydroxypropyl or 2-hydroxybutyl. When $R_3$ is alkenyl this is preferably allyl or 2-butenyl. When $R_3$ is phenylalkyl this is preferably benzyl. When $R_3O$ is hydroxy this may be acylated. $R_3$ is then preferably acetyl, propionyl or benzoyl more preferably acetyl.

$R_4$ may be hydrogen or hydroxy. When $R_4$ is hydroxy this may be acylated. $R_4$ is then preferably acetoxy, propionyloxy or benzoyloxy more preferably acetoxy. When $R_4$ is alkoxy this is preferably methoxy, ethoxy or n-propyloxy, more preferably methoxy. When $R_4$ is alkenyloxy this is preferably allyloxy.

Compounds of formula I wherein $R_4$ is other than hydrogen are preferred.

Particularly interesting compounds of formula I are those wherein, independently:

(1) $R_1$ is
  (a) mono-hydroxy- or alkoxy-substituted alkyl, i.e. hydroxyalkyl or alkoxyalkyl, especially 2-hydroxy- or 2-methoxyalkyl;
  (b) alkenyl or alkynyl, especially alkynyl, more especially 3-butynyl; and/or
  (c) (1-hydroxy- or (1-methoxy-cycloalkyl)-methyl, especially (1-hydroxy-cyclopropyl)-methyl and (1-hydroxy-cyclobutyl)-methyl, whereby hydroxy groups in $R_1$ may be optionally acylated, preferably by acetyl or propionyl, more preferably acetyl.

(2) $R_2$ is methyl,
(3) $R_3$ is hydrogen or alkyl, especially hydrogen, methyl or ethyl, and
(4) $R_4$ is hydroxy or alkoxy, especially hydroxy or methoxy.

Further preferred compounds of the formula I are those, wherein $R_2$ is methyl and $R_4$ is hydroxy and wherein:

a. $R_1$ is methyl and $R_3$ is Hydrogen, methyl, ethyl, n-propyl, allyl or 2-butenyl;
b. $R_1$ is allyl and $R_3$ is methyl;
c. $R_1$ is 3-methyl-2-butenyl and $R_3$ is methyl or ethyl;
d. $R_1$ is cyclopropylmethyl and $R_3$ is methyl; P0 e. $R_1$ is cyclobutylmethyl and $R_3$ is hydrogen, methyl, ethyl, n-propyl or allyl;
f. $R_1$ is 2-hydroxy-2-methylpropyl and $R_3$ is hydrogen, methyl or ethyl, especially hydrogen or methyl;
g. $R_1$ is 2-methoxypropyl and $R_3$ is hydrogen, methyl, ethyl or allyl;
h. $R_1$ is 2-methoxy-2-methylpropyl and $R_3$ is hydrogen, methyl or ethyl;
i. $R_1$ is (1-hydroxycyclopropyl)-methyl and $R_3$ is hydrogen, methyl, ethyl, n-propyl, n-butyl, allyl, 2-butenyl or benzyl, especially hydrogen, methyl, or ethyl;
j. $R_1$ is (1-methoxycyclopropyl)-methyl and $R_3$ is hydrogen or ethyl;
k. $R_1$ is (1-hydroxycyclobutyl)-methyl and $R_3$ is hydrogen, methyl or ethyl;
l. $R_1$ is (1-methoxycyclobutyl)-methyl and $R_3$ is ethyl;
m. $R_1$ is (1-hydroxycyclopentyl)-methyl and $R_3$ is hydrogen or methyl, especially methyl;
n. $R_1$ is tetrahydrofurfuryl and $R_3$ is methyl or ethyl, especially methyl or
o. $R_1$ is 3-butynyl and $R_3$ is hydrogen or methyl.

The compounds of formula I may exist in free base form or in the form of their acid addition salts, for example their salts with mineral acids, e.g. hydrochloric, hydrobromic or sulphuric arid, or organic acids, e.g. maleic, oxalic or tartaric acid.

The ring-system of the subject 6,7-benzomorphans contains two asymmetric carbon atoms $C_1$ and $C_5$ and, when $R_2$ is hydrogen, a third asymmetic carbon atom $C_9$. Since the iminoethane bridge between $C_1$ and $C_5$ is fixed in the cis-configuration (1,3-diaxial), if $C_1$ and $C_5$ are the only asymmetric centres, there will only be one racemate. This racemate may be resolved into optical isomers. If $C_1$, $C_5$ and $C_9$ are the only asymmetric carbon atoms, the compounds will exist as two diastereoisomers, of differing configuration at $C_9$. In accordance with nomenclature proposed by May for 5,9-dialkyl-6,7-benzomorphans [E. L. May, J. Org. Chem. 26, 188, 1621 (1961)] if the $C_9$ methyl group is in the transposition adjacent the iminoethane bridge and hence cis with respect to the substituent $OR_3$, the isomer will be referred to as the α-isomer. If the $C_9$ methyl group is in the cisposition adjacent the iminoethane bridge and hence trans with respect to $OR_3$, the isomer will be referred to as the β-isomer. The α- and β-isomers can each exist in two optically active forms, i.e. as laevo- and dextro-rotatory enantiomers. These may also be resolved to give individual isomers. The number of possible stereomeric forms will naturally increase if additional asymmetric centres are present in the side chains, e.g. in the N-substituent.

It is to be understood that the compounds of the invention as represented by formula I, include free base and acid addition salt forms as well as racemates and individual optically active isomers thereof, e.g. diastereomeric mixtures, individual diastereoisomers, D, L-racemates and individual D- and L-isomers. From the point-of-view of pharmacological activity however, the laevo-rotatory isomers are generally more active. The present invention also provides a process for the production of compounds of formula I, which comprises (A) Cyclising a compound of formula II,

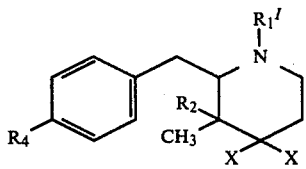 (II)

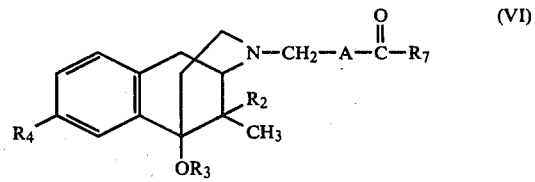 (VI)

wherein $R_1^I$ is hydrogen, alkyl or aralkyl, each X is alkoxy or both together are oxygen and $R_2$ and $R_4$ have the meanings given above, with optional ether cleavage at the 2'-position, to produce a compound of formula I, wherein $R_1$ has the meaning given above for $R_1^I$, $R_3$ is hydrogen or alkyl and $R_4$ is hydrogen, hydroxy, alkoxy or alkenyloxy, and, when desired, converting the obtained compound into another compound of the formula I by replacement or modification of a group $R_1$, $R_3$ and/or $R_4$.

Conversion of an initially obtained compound of formula I into another compound of formula I by replacement or modification of existing substituents $R_1$, $R_3$ and/or $R_4$ may be carried out by methods well known in the art of benzomorphan chemistry, e.g. in accordance with the following methods (end-steps only):

(B) reducing a compound of formula III,

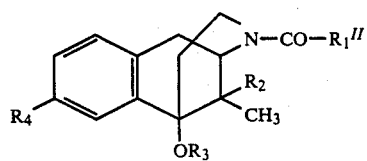 (III)

wherein $R_1^{II}$ is the remainder of an α-methylene, nonhydroxy-substituted group $R_1$ as defined above, excluding the α-carbon atom thereof, and $R_2$–$R_4$ are as defined above;

(C) reacting a compund of formula I wherein $R_1$ is hydrogen and $R_2$–$R_4$ are as defined above with a compound of formula $R_1^{III}$-Y (IV), wherein $R_1^{III}$ has the meaning given for $R_1$ excluding hydrogen and Y is a neucleophilic leaving group;

(D) reacting a compound of formula I wherein $R_1$ is hydrogen and $R_2$–$R_4$ are as defined above with a compound of formula V,

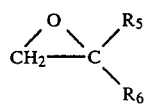 (V)

wherein $R_5$ is hydrogen, alkyl, cycloalkyl, alkoxy or aryl and $R_6$ is hydrogen or alkyl or wherein $R_5$ and $R_6$ together with the adjacent carbon atom are cycloalkyl;

(E) dealkylating or dearalkylating a compound of formula I, wherein $R_1$ is alkyl or aralkyl to obtain a compound of formula I wherein $R_1$ is hydrogen, (F) reducing a compound of formula VI, wherein A is a direct bond or is methylene, ethenylene or ethynylene and $R_7$ is hydrogen, alkyl, cycloalkyl, aryl, hydroxy or alkoxy and $R_2$–$R_4$ are as defined above;

(G) reacting a compound of formula VI as defined above with a compound of formula $R_8$-Z (VII), wherein $R_8$ is alkyl, alkenyl, alkynyl, cycloalkyl or aryl, whereby $R_7$ and $R_8$ may not simultaneously be cycloalkyl or aryl, and Z is a metal atom or metal containing radical;

(H) alkylating a compound of formula I wherein $R_1$, $R_3O$ and/or $R_4$ is, or contains, a hydroxy group;

(I) hydrogenating a compound of formula I wherein $R_3O$ or $R_4$ is alkenyloxy;

(J) hydrating a compound of formula I wherein $R_3$ is alkenyl;

(K) subjecting a compound of formula I wherein $R_1$, $R_3O$ and/or $R_4$ is, or contains, alkoxy to ether cleavage;

(L) acylating a compound of formula I wherein $R_1$, $R_3O$ and/or $R_4$ is, or contains a hydroxy group;

(M) hydrolysing or reductively cleaving a compound of formula I wherein $R_1$, $R_3O$ and/or $R_4$ is, or contains, an acyloxy group; and (N) dehydroxylating a compound of formula I wherein $R_4$ is hydroxy to obtain a compound of formula I, wherein $R_4$ is hydrogen.

It will be appreciated that the above reactions and interconversions may be conducted in any appropriate sequence. The means for carrying out the reactions (B)–(N) or obtaining the desired starting materials from compounds of formula I obtained by cyclisation reaction (A) is described in greater detail below.

In accordance with the invention it has surprisingly been found that the basic cyclisation reaction (A) can be carried out selectively to obtain specific end products using a suitable Lewis-acid, for example aluminium trichloride or boron trifluoride. In this case $R_4$ in the compound of formula II is preferably not acyloxy since this leads to undesirable side-reactions. In the starting material $R_4$ is preferably alkoxy, especially methoxy and $R_1^I$ is preferably alkyl or aralkyl, especially methyl or benzyl, more especially methyl. Depending on the reaction conditions, end products may be obtained having various, specific substituents in the 2'- and 5-positions.

On reaction of a compound of formula II, wherein $R_4$ is alkoxy and both X together are oxygen, with boron trifluoride optionally complexed with an alcohol, an ether or other suitable oxygen donor molecule, a mixture of 2'-hydroxy- and 2'-alkoxy-5-hydroxy-benzomorphan derivatives in a molar ratio of approximately 1:1 is obtained. This reaction takes place in two steps. The first step is suitably carried out in an alkanol, preferably methanol, as solvent. After removal of the solvent the obtained complex compound is boiled in an aprotic solvent, such as benzoyl, and the obtained benzomorphan derivative is isolated. Alternatively it is possible to convert the boron trifluoride complex obtained with an alkanol into a dialkylketone-acetal of formula II wherein each X is alkoxy, by reaction with an aequeous base. The dialkylketone-acetal may then be reacted in an aprotic solvent, such as dichloromethane, in the presence of boron trifluoride optionally complexed with an alkanol, such as methanol to yield the corresponding 2',5-dialkoxy-, preferably 2',5-dimethoxy-benzomorphan derivatives. By reaction of a compound of formula II, wherein both X together are oxygen and $R_4$ is alkoxy, preferably methoxy, under mild conditions and using aluminium trichloride, the corresponding 2'-alkoxy-5-hydroxy-benzomorphan derivative is obtained. This reaction is suitably conducted with benzene or nitrobenzene or mixture thereof as solvent and using 2 equivalents of aluminium trichloride.

If the latter reaction is carried out under stronger conditions, for example using more than 2 equivalents, preferably 3 equivalents, of aluminium trichloride, with longer reaction periods and at elevated reaction temperatures, formation of 2',5-dihydroxy-benzomorphan derivatives will be favoured. The reaction temperature will preferably lie between 15° and 110° C., depending on whether the 2'-alkoxy- or 2'-hydroxy-5-hydroxy-benzomorphan derivative is desired. When the cyclisation is carried out employing compounds of formula II wherein $R_4$ is hydrogen, corresponding 2'-unsubstituted-5-hydroxy- or -5-alkoxybenzomorphan derivatives are obtained.

The cyclisation reaction may also be carried out using a strong inorganic acid, especially 48% hydrobromic acid or polyphosphoric acid, in accordance with the method described in J. Med. Chem. 13, 1323 (1970), though cyclisation with a Lewis acid is generally preferred. For the cyclisation with a strong acid, temperatures between room-temperature and the boiling point of the reaction mixture are preferred. The benzomorphan derivatives obtained in this way possess a hydroxy group as $R_3O$. During the course of the cyclisation alkoxy or acyloxy substituents as $R_4$ are converted into hydroxy.

For the above described cyclisation reactions it is generally preferred to use compounds of formula II wherein $R_4$ is hydrogen or lower alkoxy. $R_1^I$ is preferably alkyl or aralkyl, especially methyl or benzyl since the reaction then proceeds more readily and leads to greater yields. In the latter case the product compounds may be dealkylated or debenzylated as herein after described (method E) and alternative N-substituents introduced in accordance e.g. with methods B to D, F and G.

In method B reduction is suitably carried out using diborane or a complex hydride having a large reduction capacity, such as lithium aluminium hydride. The hydride may be employed in equimolar amounts or in excess. The reduction is preferably carried out in an inert solvent, particularly tetrahydrofuran, at a temperature between 0° C. and the boiling point of the solvent.

The starting compounds of formula III for use in this process may be obtained by reacting a compound of formula I wherein $R_1$ is hydrogen with an acylhalide of formula $R_1^{II}$-CO-Hal (VIII) wherein $R_1^{II}$ has the meaning already given and Hal is halogen, preferably chlorine, or with the corresponding carboxylic acid anhydride. The acylation is preferably carried out in the presence of an acid-binding agent, in particular triethylamine or pyridine. Suitable solvents are e.g. chloroform, pyridine or dimethyl formamide. The reaction temperature is generally between 0° and the boiling point of the reaction mixture. If the acylation is carried out using a carboxylic acid anhydride in the presence of orthophosphoric acid, hydroxy groups present as $R_4$ and $R_3O$ will be acylated, without acylation at the 2-position.

Compounds of formula III may also be obtained by reaction of a compound of formula I wherein $R_1$ is hydrogen with a compound of formula $R_1^{II}$-CO-OH (IX) wherein $R_1^{II}$ has the meaning already given, in the presence of e.g. dicyclohexylcarbodiimide, preferably in chloroform as solvent.

It will be apparent that method B is not suitable for all possible substituents $R_1$, $R_3$ and $R_4$. Thus $R_1^{II}$ in the starting materials, e.g. of formula IX, used to obtain the compounds of formula III should not contain hydroxy groups. Compounds of formula III containing hydroxy groups can however be obtained using the corresponding starting materials wherein the hydroxy group is replaced by acyloxy and hydrolysing these in the product. If compounds of formula III wherein $R_4$ is acyloxy and/or $R_1^{II}$ contains an acyloxy group are reduced these will usually be converted into hydroxy.

In method C, Y in the compound of the formula IV is preferably halogen, in particular chlorine, bromine or iodine, or an aryl-, aralkyl- or alkylsulfonyloxide group, in particular methoxy or tosyloxy. The reaction is preferably carried out using equimolar amounts or a small excess of the compound of formula IV. Suitably the reaction is conducted in the presence of an acid-binding agent which does not react with the compound of formula IV, for example sterically hindered amines, such as dicyclohexylethylamine and especially inorganic bases such as sodium or potassium carbonate and in particular sodium or potassium bicarbonate. The reaction is preferably conducted in an inert organic solvent, tetrahydrofuran or dimethylformamide or mixtures thereof being preferred, at reaction temperatures between 0° C. and the boiling point of the solvent. With less reactive compounds IV, the reaction may be accelerated by the addition of catalytic or equivalent amounts of sodium or potassium iodine.

Method D is suitably carried out in an inert organic solvent, preferably a lower alkanol of 1-5 carbon atoms or in mixtures of solvents such as dichloromethane and methanol. The presence of minor quantities of water may be advantageous. The reaction conditions are determined largely by the reactivity of the epoxide of formula V. The reaction generally takes several hours and is preferably conducted at a temperature of 40°-120° C. Owing to the volatility of the epoxide the reaction is preferably conducted in a closed reaction vessel.

Method E can for example be carried out using cyanogen bromide in accordance with the Brown method [c.f. H. A. Hageman, Org.-React. 7, 198 (1953) and K. W. Bentley, Techniques of Organic Chemistry 11, 773 (1963)] or with a chloroformic acid ester or by catalytic debenzylation. The first 2 methods are only appropriate when there is no hydroxy group in the 2' position.

The reaction is preferably carried out using a chloroformic acid-alkyl- or -phenyl-ester generally the ethylester, and the obtained product is saponified and decarboxylated. The saponification and decarboxylation can be carried out in e.g. an alcoholic alkaline medium, preferably with calcium hydroxide in n-butanol.

Method F may be carried out using a hydride, e.g. lithium aluminium hydride or sodium borohydride as reducing agent. Catalytic hydrogenation using e.g. platinum or palladium as catalyst in a solvent such as methanol, ethanol or acetic acid or Raney-nickel as catalyst in an alkanol as solvent may also be employed to reduce carbonyl compounds to secondary alcohols.

When $R_7$ in the compound of formula VI is hydrogen, hydroxy or alkoxy compounds of formula I are obtained having a primary alcohol residue in the substituent $R_1$. When $R_7$ is alkyl, cycloalkyl or aryl the corresponding secondary alcohol derivatives are obtained. When $R_4$ and/or $OR_3$ in the compound of formula VI are acyloxy these groups will generally be converted to hydroxy. In general method F is less suitable for obtaining compounds of formula I wherein $R_1$, $R_3$ and/or $R_4$ contain one or more unsaturated linkages, since it will lead to the formation of side-products in which these are saturated.

Reaction G may be carried out in accordance with known methods preferably in an inert solvent such as tetrahydrofuran or diethylether and under an inert atmosphere. For this method A in the compound of formula VI is preferably a direct bond and Z in the compound of formula VII is preferably lithium, —MgCl or —MgBr. When $R_4$ in the starting material of formula VI is acyloxy this will simultaneously be converted to hydroxy.

The starting compounds of formula VI for methods F and G may be prepared by reacting a compound of formula I wherein $R_1$ is hydrogen with a compound of formula $R_7$-CO-A-CH$_2$-Hal (X) wherein Hal, $R_7$ and A have the meanings already given. The reaction is conducted analogously to that already described for method C. Compounds of formula VI wherein $R_7$ is alkyl or aryl may also be obtained by reaction of the corresponding carboxylic acid, carboxamide or carbonitrile [—C(O)$R_7$ represents e.g. —COOH, —CONH$_2$ or —CN] with a suitable organometallic compound of the formula VII, as hereinbefore defined.

The methods H—M may be carried out using a compound of formula I obtained via the initial cyclisation reaction method A, or a compound of formula I obtained according to any of methods B-G, as starting material.

Compounds of formula I obtained according to method A wherein $R_3$ is hydrogen and $R_4$ is hydrogen or alkoxy may be converted into the corresponding compounds wherein $R_3$ is alkyl, alkenyl, alkynyl or aralkyl by conversion first into the alkali metal alkoxide, for example with sodium hydride, and reacting the alkali metal alkoxide with an alkyl-, alkenyl-, alkynyl- or aralkylhalide (method H). Especially suitable solvents for both process steps are aprotic organic solvents, e.g. tetrahydrofuran, dimethylformamide, or toluene. The reaction conditions will depend upon the reactivity of the reaction partners. Generally the temperature will be between 15° C. and the boiling point of the solvent and the reaction time will be generally between 2 and 48 hours.

The speed of the reaction decreases with increase in the molecular weight of the alkylating agent. Compounds of formula I wherein $R_3$ is n-propyl or a larger alkyl group are therefore preferably obtained by catalytic hydrogenation of the corresponding compound wherein $R_3$ is 2-alkenyl (method I), since the latter are more readily obtained owing to the greater reactivity of the 2-alkenyl-halides.

Obtained compounds of formula I wherein $R_3$ is alkenyl can advantageously be converted into the corresponding compounds wherein $R_3$ is hydroxyalkyl by hydration, e.g. by reaction with diborane followed by hydrogen peroxide/sodium hydroxide (method J). In this manner e.g. 5-allyloxybenzomorphan derivaties may be converted to the corresponding 5-(3-hydroxypropoxy) derivatives.

Obtained compounds of formula I wherein $R_3$ is alkyl, alkenyl, alkynyl, aralkyl or hydroxyalkyl and/or $R_4$ is alkoxy may be converted by selective ether cleavage into the corresponding compounds wherein $R_4$ is hydroxy (method K). Ether cleavage may be effected using e.g. an alkali metal-thioalkoxide, e.g. sodiumthioethoxide, in an aprotic solvent such as dimethylformamide, at a temperature of between 100° and the boiling point of the reaction mixture. Provided the group $R_3O$ of the starting material is resistant to aluminium trichloride or boron tribromide, e.g. as in the case of alkoxy, these reagents too may be used for selective ether-splitting in the 2'-position. Preferably the reaction is carried out using boron tribromide in dichloromethane as a solvent at a temperature of from −10° C. to the boiling point of the reaction mixture. When starting materials are employed in which $R_3O$ is hydroxy, still stronger methods may be employed, e.g. splitting using 47% hydrobromic acid.

Compounds of formula I wherein $R_3O$ and $R_4$ are the same and are both alkoxy or acyloxy may be prepared from corresponding compounds wherein $R_3O$ and $R_4$ are hydroxy. Such dialkoxy compounds may be obtained as described above according to method H. In place of an alkylhalide it is also possible to use an alkenylhalide and to reduce the obtained compound wherein $R_3O$ and $R_4$ are both alkenyloxy according to method I. The reduction is preferably carried out using a palladium or palladium/charcoal catalyst. If desired an alkoxy group $R_4$ in the obtained compound may be converted into hydroxy in accordance with method K. Acylation of hydroxy groups $R_3O$ and $R_4$ (method L) may be carried out e.g. using a carboxylic acid anhydride or acid chloride in the presence of an acid-binding agent, preferably triethylamine or pyridine. Suitable solvents for the reaction are e.g. chloroform, pyridine or dimethylformamide. Reaction temperature is between 0° C. and the boiling point of the reaction mixture. The acylation using a carboxylic acid anhydride is however preferably carried out using the anhydride itself as solvent and with the addition of orthophosphoric acid. In this case the reaction temperature is preferably about 60° C.

Acyloxy groups as $R_4$ can readily be selectively hydrolysed, e.g. in aequeous solution, to yield the corresponding 2'-hydroxy-5-acyloxy compounds of formula I (method M). In view of the phenolic nature of the 2'-hydroxy group this may readily be selectively alkylated or acylated in accordance with methods H and M.

When compounds of formula I are desired in which $R_4$ is hydroxy, the preferred synthesis proceeds via cyclisation (method A) to obtain compounds of formula I wherein $R_1$ is alkyl or aralkyl and $R_4$ is alkoxy, dealkylation or dearalkylation (method E) to obtain corresponding compounds wherein $R_1$ is hydrogen, ether cleavage (method K) to convert $R_4$ into hydroxy, and introduction of further substituents at the N-atom (methods B-D, F and G)

Compounds of formula I having a hydroxy-containing substituent $R_1$ may be alkylated to give the corresponding compounds in which the hydroxy is replaced by alkoxy. Alkylation is conveniently carried out according to method H as hereinbefore described. When the starting material contains more than one hydroxy group, e.g. when $R_4$ is hydroxy, these will generally be simultaneously converted into alkoxy groups. By virtue of the varing reactivity of the hydroxy groups in positions 2', 5 and on the N-substituent $R_1$, hydroxy groups as $R_1$ or both as $R_4$ and in $R_1$ may, if desired, be selectively alkylated. A hydroxy group $R_4$ can for example be selectively alkylated by reacting with a dilute alkali-metal hydroxide solution, in the presence of an alkali-metal salt and reacting the obtained compound with a dialkylsulphate. Hydroxy groups as $R_4$ and hydroxy groups in $R_1$ may also be selectively alkylated taking advantage of the degree of steric hindrance for hydroxy groups $R_3O$ and in $R_1$, e.g. by careful alkylation of a hydroxy group in $R_1$ using e.g. a calculated amount of alkylating agent.

Compounds of formula I having an acyloxy group in the substituent $R_1$ may also be obtained from the corresponding hydroxy compounds by acylation e.g. according to method L as hereinbefore described. Hydroxy groups e.g. as $R_3O$ and $R_4$ will generally also be acylated. Selective acylation, as alkylation, is also possible taking advantage of the varying reactivities of the hydroxy groups.

Compounds of formula I wherein $R_1$ contains a hydroxy group may be obtained from corresponding compounds wherein $R_1$ contains an alkoxy substituent via ether-cleavage in accordance with method K. Suitable agents for ether-cleavage are hydrobromic acid and Lewis-acids such as boron tribromide. Depending on the choice of reagent, alkoxy groups as $R_3O$ and $R_4$ may also be converted to hydroxy. Selective cleavage of aromatic ether groups may be carried out using e.g. alkali-metal thioalkoxides such as sodium thioethoxide.

Compounds of formula I wherein $R_1$ contains a hydroxy group may also be obtained by hydrolysis of corresponding compounds wherein $R_1$ contains an acyloxy group in accordance with method M, e.g. by acid or alkaline hydrolysis, preferably in an aequeous, alcoholic or aequeous-alcoholic medium. Such acyloxy groups may also be removed by reductive cleavage, e.g. using complex hydrides and proceeding analogously to method B. When $R_3O$ as $R_4$ are acyloxy these will generally be simultaneously converted to hydroxy. Acyloxy groups as $R_4$ may be selectively hydrolysed, e.g. using a dilute solution of hydrochloric acid in methanol or ethanol, taking advantage of the fact that these are generally less stable to hydrolysis than acyloxy groups in $R_1$.

Compounds of formula I wherein $R_4$ is hydrogen may also be obtained by dehydroxylation of the corresponding compounds wherein $R_4$ is hydroxy (method N), e.g. by reaction with 1-phenyl-5-chlorotetrazole or with dicyclohexylcarbodiimide, and catalytic reduction of the obtained reaction product [c.f. W. J. Musliner and J. W. Gates, J. Amer. Chem. Soc. 88, 4271 (1966), H. C. Beyerman et al., Rec. trav. chim. 95, 43 (1976) and E. Vowinkel and C. Wolff, Chem. Ber., 107, 907 (1974)].

The obtained products from methods A-N may be isolated and purified by conventional means, e.g. by column chromatography, before crystalisation in and addition salt or free base form.

Diastereomers may be separated by known techniques, based on their varying chemical and physical properties e.g. using fractional crystalisation or column chromatography. Separation of isomers may be carried out on the end product or at an earlier stage during synthesis. Racemic mixtures may be resolved into their optical isomers, e.g. by separating their salts with appropriate optically active acids, e.g. camphorsulphonic acid.

From the foregoing description it will be apparent that, in addition to their pharmacological activity as hereinafter described, many of the compounds of formula I are also useful as intermediates in the synthesis of further formula I derivatives.

The starting materials of formula II wherein $R_2$ is hydrogen are known from Japanese Patent Application No. 75.58072 [Chemical Abstracts 87, 53468 (1977)]. Compounds of formula II wherein $R_2$ is methyl are known from e.g. Dutch Patent Specifications Nos. 69.08527 and 69.08528 and the corresponding U.K. Patent Specification No. 1,299,669. Other starting materials of formula II may be prepared analogously.

The compounds of formula I possess pharmacological activity. In particular they are useful as analgesic and narcotic antagonist agents as well as luteinising hormone (LH) secretion inhibiting agents, as indicated in the following test methods:

Analgesic activity

1. The tail retraction test in the rat. The method, employing male Wistar rats, is as described in Arzneim. Forsch. 13, 502 (1963), the measuring time of 15 seconds being reduced to 10 seconds. The results are graded according to the following scale:
   (A) moderate pain killing activity (MA): tail-retraction time 6 to 10 seconds;
   (B) pronounced pain killing activity (PA): no tail-retraction within 10 seconds, but slight motion of tail in hot water;
   (C) surgical pain killing activity (SA): no tail-retraction within 10 seconds and no motion in hot water.
   Positive results are obtained in this test method using compounds of formula I at a dosage of e.g. 0.01 to 10 mg/kg s.c..
2. Writhing test in the rat. The test substance is administered s.c. 30 minutes before or p.o. 45 minutes before i.p. injection of 1 ml of 1% acetic acid into female Wistar rats of average body weight 150–190 g, and the number of writhes performed during the following 25 minutes are recorded. The results are compared with those obtained on i.p. injection of 1% acid into untreated controls.
   Positive results are obtained in this test, using compounds of formula I at a dosage of e.g. 0.001 to 10 mg/kg s.c. and 0.1 to 100 mg/kg p.o.

For analgesic use the dosage will, of course, vary depending on the compound employed, the mode of administration and the treatment desired. In general satisfactory results are obtained on administration at a daily dosage of from about 0.001–10 mg/kg animal body weight, conveniently given in divided doses 2 to 4 times a day or in sustained release form. For mammals the total daily dosage is in the range of from about 1 mg, preferably about 10 mg, to about 250 mg, more preferably from about 10 to about 100 mg, and dosage forms suitable for oral administration comprise from about 0.25 mg, preferably about 2.5 mg, to about 100 mg, more preferably from about 2.5 to about 50 mg of compound of formula I.

Narcotic antagonist activity

Fentanyl antagonism test in the rat. 0.63 mg/kg of fentanyl is administered s.c. to male Wistar rats to induce respiration depression, loss of righting reflex, muscle stiffening, killing of surgical pain and blocking of corneal- and pinna-reflexes. The ability to counteract these phenomena is a measure of narcotic antagonist activity of a test-compound. 30 minutes after fentanyl administration, the test-animals are injected i.v. with the test compound or with pentazocine or nalorphine as controls.

Positive results are obtained in this test using compounds of formula I at a dosage of e.g. 0.001 to 10 mg/kg s.c.

In accordance with the above test compounds of formula I are indicated as useful for the treatment of narcotic, e.g. morphine, overdose. The test further indicates that the compounds themselves possess no or only slight narcotic activity. Suitable dosages and unit dosage forms for narcotic antagonist use are as hereinabove described for analgesic use.

LH-secretion inhibiting activity

1. Ovulation inhibition in the rat. Adult female rats of the Ivanovas strain each weighing 200–250 g are maintained under standard conditions [14 hours light (0.4.00–18.00 h), 24° C. and 55–60% relative humidity] and allowed access ad libitum to food and water. Animals with a proven, regular 4day oestrus cycle receive the test compound either subcutaneously or orally during the pro-oestrus phase, the doses being administered once at 13.00 h and again at 16.00 h. 20 Hours after the first dose, the rats are sacrificed, the fallopian tubes exposed and the total number of ova in both tubes counted with a disecting microscope. Ovulation is considered to have been inhibited only when no ova are found. Five rats are used per dose. Positive results are obtained in this test using compounds of formula I at a dosage of e.g. $2\times0.0005$ to $2\times1$ mg/kg s.c. and $2\times0.05$ to $2\times3.0$ mg/kg p.o..

2. Ovulation inhibition in the hamster. The above described method is repeated using adult, female golden hamsters (Mesocricetus auratus, Füllindsdorf) weighing ca. 100 g and with administration of the test compound s.c. in three doses during prooestrus at 11.00, 13.00 and 16.00 h. The animals are sacrificed 22 hours after the first injection.

Positive results are obtained in this test using compounds of formula I at a dosage of e.g. $3\times0.005$ to $3\times0.3$ mg/kg s.c.

3. LH-serum assay in the rat. Female rats of the Ivanovas Wistar strain are ovariectomised under Evipan anaesthesia. Twenty days after recovery, the test compound is administered s.c. at varying dosages. One hour after administration, the rats are decapitated and the serum LH level determined using standard radioimmunoassay techniques. Five rats are used per dose and the mean level of luteinising hormone found in the animals expressed as a percentage of the mean level obtained in solvent-treated controls. Positive results are obtained in this test using compounds of formula I at a dosage of e.g. 0.01 to 10 mg/kg s.c.

In view of their LH-secretion inhibiting activity, compounds of formula I are useful in the treatment of disorders having an aetiology associated with or modulated by LH-secretion or having an aetiology in which the pysiological regulation of LH-secretion is implicated e.g. in the treatment of prostate hypertrophy or in the treatment of menopausal syndrome, in particular post-menopausal hot flashes e.g. in accordance with the studies reported by Tataryn et al. ["Thermoregulatory Mechanisms and their Therapeutic Implications, 4th. Int. Symp. on the Pharmacology of Thermoregulation, Oxford, 1979" published by Karger, Basel 1980, pp. 202–207] and Casper et al. ["Science", 205, pp. 823–825 (1979)].

The amount of compound administered in accordance with this aspect of the invention will again vary according to e.g. particular compounds employed, mode of administration, condition to be treated and therapy desired.

In general satisfactory results are obtained depending on the mode of administration, e.g. s.c. or oral, with a daily dosage of from about 0.001 to about 1.0 mg/kg. Conveniently the compound is presented in unit dosage form administered 2 to 4 times a day or in sustained release form.

For larger mammals a suitable oral daily dosage is from about 0.1, preferably about 0.5 mg, to about 20, preferably about 4.0 mg, and a suitable unit dosage form contains about 0.025, preferably about 0.125, to about 10, preferably about 2 mg, of compound of formula I.

For use in accordance with the methods of the invention the compounds of formula I may be administered in free base form or in pharmaceutically acceptable acid addition salt form, which salt forms generally have the same order of activity as the free base forms.

The compounds of formula I may also be administered in optically active or racaemic form.

The compounds of formula I may be admixed with conventional pharmaceutically acceptable diluents or carriers and, optionally, other excipients and administered for example in such forms as tablets, capsules, powders and injectable solutions. They may be administered in combination preparations with other analgesics or with other active agents such as sedatives, tranquilizers or hypnotics.

In accordance with the foregoing the present invention also provides (i) a method of alleviating pain or of inhibiting luteinising hormone secretion (in particular of treating prostatic hypertrophy or menopausal syndrome, especially post-menopausal hot flashes) in a subject in need of such treatment, which method comprises administering to said subject an effective amount of a compound of formula I, as well as (ii) pharmaceutical compositions comprising a compound of formula I as active ingredient.

EXAMPLE 1

(a) 5-hydroxy-2'-methoxy-2,9,9-trimethyl-6,7-benzomorphanhydrochloride

A mixture of 59.5 g (0.2 Mol) 2-(4-methoxybenzyl)-1,3,3-trimethyl-4-piperidone hydrochloride and 53.8 g (0.4 Mol) of aluminum trichloride in 54 g nitrobenzene and 1500 ml of dry benzene are boiled under reflux for 1 hour. After cooling the reaction mixture is extracted with 750 ml 4 N sodium hydroxide solution, the temperature being maintained below 35° C. The organic phase is separated and extracted with 750 ml 1 N hydrochloric acid. The acid aqueous phase is rendered alkali by the addition of 100 ml 25% ammonia and extracted three times with 250 ml chloroform. The collected chloroformic phases are dried with sodium sulphate and evaporated under reduced pressure. The residue, 46.7 g, is converted into the hydrochloride by reaction with isopropanol/HCl and crystallized from a mixture of methanol and ethylacetate. 44.6 g of the title compound are obtained, m.p. 233°–236° C. (with decomposition).
(b) Starting from 3,3-dimethyl-2-(4-methoxy-benzyl)-4-piperidone, 9,9-dimethyl-5-hydroxy-2'-methoxy-6,7-benzomorphan hydrochloride is obtained analogously, m.p. 215°–218° C. (with decomposition).
(c) Proceeding analogously and starting from 2-(4-methoxybenzyl)-1,3-dimethyl-4-piperidone and after separation of the 2 obtained isomers by crystallisation there is obtained:
  (1) 2,9α-dimethyl-5-hydroxy-2'-methoxy-6,7-benzomorphan hydrochloride, m.p.: 252°–253° C.
  (2) 2,9β-dimethyl-5-hydroxy-2'-methoxy-6,7-benzomorphan hydrochloride, m.p.: 288°–289° C.

EXAMPLE 2

2',5-dihydroxy-2,9,9-trimethyl-6,7-benzomorphan

A mixture of 59.5 g (0.2 Mol) of 2-(4-methoxybenzyl)-1,3,3-trimethyl-4-piperidone hydrochloride and 80.1g (0.6 Mol) of aluminium trichloride in 80 g of nitrobenzene and 1500 ml of dried benzene are stirred for 30 minutes at room temperature and subsequently for five hours with boiling under reflux. The obtained benzomorphan/aluminium trichloride complex crystallizes out. After cooling to 15° C., 1500 ml of an ice-cold 2 N hydrochloric acid solution is added. After filtration the acid aqueous phase is separated from the organic phase and rendered basic by the addition of 780 ml 25% ammonia. The obtained solution is extracted three times with 500 ml of a mixture of chloroform and n-butanol (8:2). The collected organic phases are dried over sodium sulphate and evaporated under reduced pressure. The crystalline product, 51.4 g is recrystallized from ethylacetate. There are obtained 35.1 g of the title compound, m.p.: 161° C. (with decomposition). (Note: The substance contains 0.5 Mol ethylacetate).

EXAMPLE 3

5-hydroxy/methoxy-2'-methoxy-2,9,9-trimethyl-6,7-benzomorphan hydrochloride 66 ml of borontrifluoride/methanol complex are added with stirring over a period of 30 minutes to a solution of 52.2 g (0.2 Mol) of 2-(4-methoxybenzyl)-1,3,3-trimethyl-4-piperidone in 220 ml of methanol, the temperature being maintained below 35° C. After stirring for 16 hours at room-temperature the reaction mixture is evaporated under reduced pressure. Evaporation is repeated after the addition of toluene, so as to remove all methanol present.

The residue, 130 g, is dissolved in 500 ml dry benzene and boiled under reflux with stirring for 9 hours. During the course of the reaction 250 ml benzene and all volatile components are removed by distillation. The volume of the reaction mixture is kept constant by the steady addition of 250 ml of benzene. The obtained reaction mixture is extracted after cooling, by addition of 66 g pulverized sodium hydroxide and after a further 30 minutes of 300 ml of water. The benzene and the aequeous phases are separated. The aequeous phase is extracted twice with 250 ml of chloroform. The collected organic phases are dried over sodium sulphate and evaporated under reduced pressure. The residue, comprising of 55.0 g of an ±1:1 mixture of the title compound is converted into the HCl salt and crystallized from a mixture of methanol and ethyl acetate, m.p.: 183°–190° C. (with decomposition).

Half of the mixture so obtained is converted into the corresponding 2',5-dihydroxy-6,7-benzomorphan derivative according to the process hereinafter described in example 7. The other half is converted into the corresponding 2',5-dimethoxy-6,7-benzomorphan derivative according to the method hereinafter described in example (8a).

EXAMPLE 4

2',5-dimethoxy-2,9,9-trimethyl-6,7-benzomorphan hydrochloride 40 ml of borontrifluoride etherate are added drop-wise over 20 minutes and with stirring to a solution of 52.2 g (0.2 Mol) 2-(4-methoxybenzyl)-1,3,3-trimethyl-4-piperidone in 500 ml methanol, the temperature being maintained below 35° C. After stirring for 16 hours at room-temperature 40 g pulverized sodium hydroxide are added. After stirring for a further 30 minutes the obtained sodium salts are filtered off and washed with methanol. The filtrate is evaporated under reduced pressure and after addition of 500 ml water, extracted 3 times with 150 ml of chloroform. The chloroform phases are dried over sodium sulphate and evaporated under reduced pressure. After crystallization from 200 ml petrol ether (b.p.: 60°–80° C.) and further recrystallization there are obtained 25.4 g 4,4-dimethoxy-2-(4-methoxybenzyl)-1,3,3-trimethylpiperidine, m.p.: 91°–92.5° C.

A solution of 18.0 g (0.056 Mol) of the obtained 4,4-dimethoxy compound in 90 ml of dry benzene is added drop-wise at room-temperature over 4½ hours to a mixture of 60 ml benzene and 2.4 ml methanol saturated with borontrifluoride. After boiling under reflux for 6 hours, 20 g of pulverized sodium hydroxide are added. After stirring for a further 30 minutes the sodium salts are filtered off, the filtrate evaporated under reduced pressure, 200 ml of water added and the obtained mixture shaken 3 times with 100 ml of chloroform. The collected chloroform extracts are dried over sodium sulphate and evaporated under reduced pressure. The residue, 22.3 g, is chromatographed over 500 g SiO$_2$ using toluene/methanol (3:1) as eluent. The fractions containing the desired product are collected, evaporated under reduced pressure and converted into the corresponding hydrochloride. After crystallization from 25 ml methanol/acetone (1:9) there are obtained 4.64 g of the title compound, m.p.: 210°–212° C. (with decomposition).

EXAMPLE 5

2',5-dihydroxy-2,9,9-trimethyl-6,7-benzomorphan

A solution of 59.5 g (0.2 Mol) of 2-(4-methoxybenzyl)-1,3,3-trimethyl-4-piperidone hydrochloride in 600 ml of 47% hydrobromic acid is boiled under reflux for 16 hours, the initially obtained volatile components being distilled off until a boiling point of 124° C. is attained. After cooling, the reaction mixture is diluted with 600 ml of water, if necessary filtered, and poured into 500 ml of 25% ammonia and 250 g ice. After extracting 3 times with 200 ml of chloroform/butanol (8:2) followed by evaporation under reduced pressure there are obtained 48.3 g of the raw product. The raw product is chromatographed over 750 g of aluminium oxide using chloroform/methanol (95:5) as eluent. 14.8 g of the title compound are obtained, m.p. 184°–188° C.

EXAMPLE 6

5-hydroxy-2'-methoxy-2,9,9-trimethyl-6,7-benzomorphan hydrochloride 316 g of sodium hydroxide are added to a solution of 49.4 g (0.2 Mol) of 2',5-dihydroxy-2,9,9-trimethyl-6,7-benzomorphan in 1500 ml of water and a further 135 g (1.07 Mol) of dimethylsulphate are then added drop-wise over 45 minutes at 80°-85° C. After warming for 5 hours at approximately 80° C. the reaction mixture is cooled and extracted twice with 500 ml of chloroform. The collected chloroformic phases are dried over sodium sulphate and evaporated under reduced pressure. The residue is converted into the hydrochloride and crystallized from a mixture of methyl and ethylacetate to yield 46.4 g of the title compound. The product is identical with the compound obtained in accordance with example (1a).

EXAMPLE 7

2',5-dihydroxy-2,9,9-trimethyl-6,7-benzomorphan

A solution of 31.1 g (0.1 Mol) of 2',5-dimethoxy-2,9,9-trimethyl-6,7-benzomorphan hydrochloride (c.f. example 4) in 150 ml 47% hydrobromic acid is boiled for ½ hour under reflux. After cooling the solution is diluted with 150 ml of water and poured on to 450 g of ice and 150 ml 25% ammonia. The obtained crystals are filtered off, washed with water and dried under vacuum. In this way there are obtained 24.4 g of the title compound, m.p.: 174°-177° C. The crystals contain 1 Mol of water of crystallization.

EXAMPLE 8

2',5-dimethoxy-2,9,9-trimethyl-6,7-benzomorphan hydrochloride (a) 21.8 g (0.5 Mol) of a 55% dispersion of sodium hydride in oil are added to 52.2 g (0.2 Mol) of 5-hydroxy-2'-methoxy-2,9,9-trimethyl-6,7-benzomorphan (c.f. example 1a) in 500 ml of dry peroxide-free tetrahydrofuran, followed by the drop-wise addition over 45 minutes of 142 g (1.0 Mol) of methyliodide, and the mixture is stirred for 4 hours at room-temperature. 9 ml of water are added carefully to the obtained reaction mixture and the tetrahydrofuran is evaporated off under reduced pressure. After addition of 250 ml of water the residue is extracted 3 times with 250 ml of chloroform. The combined chloroformic phases are dried over sodium sulphate and concentrated under reduced pressure. The residue is converted into the hydrochloride, washed with toluene to remove paraffin oil and crystallized from methanol/ethylacetate. There are obtained 53.5 g of the title compound, m.p.: 212°-214° C. (with decomposition).

(b) Starting from 2',5-dihydroxy-2,9,9-trimethyl-6,7-benzomorphan (c.f. example 2) and proceeding analagously to example 8a using twice the amount of sodium hydride and methyliodide there is again obtained 2',5-dimethoxy-2,9,9-trimethyl-6,7-benzomorphan hydrochloride.

(c) On repeating example 8b using ethyliodide in place of methyl iodide and with reaction at boiling temperature instead of room-temperature there is obtained after recrystallization from acetone/methanol (9:1), 2',5-diethoxy-2,9,9-trimethyl-6,7-benzomorphan hydrochloride, m.p.: 206°-208° C.

(d) Proceeding analagously to example 8c, using allylbromide instead ethyliodide and with a reaction period of 6 hours there is obtained 2',5-diallyloxy-2,9,9-trimethyl-6,7-benzomorphan as a non-crystalline base.

(e) Proceeding analagously to example 8c, with 5-hydroxy-2'-methoxy-2,9,9-trimethyl-6,7-benzomorphan (c.f. example 1a) there is obtained 5-ethoxy-2'-methoxy-2,9,9-trimethyl-6,7-benzomorphan as a non-crystalline base.

(f) Proceeding analagously to example 8d using 5-hydroxy-2'-methoxy-2,9,9-trimethyl-6,7-benzomorphan (c.f. example 1a) there is obtained 5-(allyloxy)-2'-methoxy-2,9,9-trimethyl-6,7-benzomorphan hydrochloride, m.p.: 207°-209° C.

(g) Proceeding analagously to example 8f using 2-butenyl bromide in place of allylbromide there is obtained 5-(2-butenyloxy)-2'-methoxy-2,9,9-trimethyl-6,7-benzomorphan hydrochloride, m.p.: 210°-212° C.

(h) Proceeding analagously to example 8f, using benzyl-bromide in place of allylbromide there is obtained 5-benzyloxy-2'-methoxy-2,9,9-trimethyl-6,7-benzomorphan hydrochloride, m.p.: 185°-189° C.

EXAMPLE 9

2',5-di-n-propoxy-2,9,9-trimethyl-6,7-benzomorphan hydrochloride (a) A solution of 2.98 g (9.1 mMol) of 2',5-diallyloxy-2,9,9-trimethyl-6,7-benzomorphan (c.f. example 8d) in 70 ml abs. ethanol are hydrogenated at room-temperature under normal pressure using 300 mg Pd/C (5%) as catalyst. After uptake of the calculated amount of hydrogen the catalyst is filtered off and the filtrate concentrated under reduced pressure. The residue is converted into the hydrochloride and crystallized from methanol/acetone (1:9). 2.1 g of the title compound are obtained, m.p.: 190°-193° C. (with decomposition).

The 2,9,9-trimethyl-6,7-benzomorphan derivatives shown in the following table are obtained analagously:

| No. | Starting material according to example | 2'-Subst. obtained | 5-Subst. product | Salt | m.p. (°C.) |
|---|---|---|---|---|---|
| b | 8f | $OCH_3$ | $OC_3H_7(n)$ | base | oil |
| c | 8g | $OCH_3$ | $OC_4H_9(n)$ | HCl | 213-216 |

EXAMPLE 10

2'-hydroxy-5-(3-hydroxypropoxy)-2,9,9-trimethyl-6,7-benzomorphan hydrochloride (a) 24 ml of a 1 M diborane solution in tetrahydrofuran are added drop-wise over 2 hours at a temperature of −10° C. to a solution of 2.02 g (6 mMol) of 5-allyloxy-2'-methoxy-2,9,9-trimethyl-6,7-benzomorphan hydrochloride (c.f. example 8f) in 25 ml of tetrahydrofuran. After stirring for 4 hours at room-temperature 16 ml of a 1 N sodium hydroxide solution and 2 ml 30% hydrogen peroxide are carefully added drop-wise. After reaction for 1 hour at room-temperature, 30 ml 1 N hydrochloric acid are added and the mixture is boiled for a further 1 hour under reflux. The tetrahydrofuran is distilled off under reduced pressure, the acid aqueous phase rendered alkali with 25% ammonia and extracted 3 times with 25 ml chloroform. The combined chloroformic phases are dried over magnesium sulphate and concentrated under reduced pressure. After conversion of the residue into the hydrochloride and crystallition from methanol/ether acetate 1.15 g of the title compound are obtained, m.p.: 187°–193° C.

(b) Starting from 5-(2-butenyloxy)-2'-methoxy-2,9,9-trimethyl-6,7-benzomorphan hydrochloride (c.f. example 8g) there is obtained 5-(2-hydroxybutoxy)-2'-methoxy-2,9,9-trimethyl-6,7-benzomorphan as the free base. This may be reacted further without purification.

EXAMPLE 11

(a) 2',5-dimethoxy-9,9-dimethyl-6,7-benzomorphan hydrochloride

A solution of 4.68 g (44 mMol) cyanogenbromide in 28 ml chloroform are added drop-wise within 5 minutes to a solution of 8.25 g (30 mMol) 2',5-dimethoxy-2,9,9-trimethyl-6,7-benzomorphan (c.f. example 8a) in 20 ml dry ethanol-free chloroform. After boiling for 4 hours under reflux the solution is concentrated under reduced pressure, the residue dissolved in 150 ml toluene, washed twice with 50 ml 2 N hydrochloric acid and once with water, dried over sodium sulphate and evaporated to dryness under reduced pressure to yield 7.82 g 2-cyano-2',5-dimethoxy-2,9,9-trimethyl-6,7-benzomorphan. The obtained residue is dissolved in 40 ml of dry peroxide-free tetrahydrofuran and the solution added drop-wise under a nitrogen atmosphere over a period of 20 minutes to a suspension of 2,10 g (61.7 mMol) of lithium aluminum hydride in 85 ml tetrahydrofuran. After boiling for 3 hours under reflux and cooling, 2.1 ml water, 1.6 ml 4 N sodium hydroxide solution, 7.3 ml water and 85 ml chloroform are added sequentially. After stirring for 30 minutes the obtained hydroxide is filtered off over hyflo. The precipitate is stirred 3 times with 50 ml chloroform/butanol (9:1). The filtrated washed with water, dried over sodium-sulphate and concentrated under reduced pressure. The residue is converted into the hydrochloride and crystallized from methanol/ethylacetate to yield 4.9 g of the title compound, m.p.: 220°–222° C. (with decomposition).

(b) 9,9-dimethyl-5-hydroxy-2'-methoxy-6,7-benzomorphan hydrochloride 261 g (1 Mol) of 5-hydroxy-2'-methoxy-2,9,9-trimethyl-6,7-benzomorphan (c.f. example 1) are dissolved in 1250 ml of chloroformic acid ethylester and boiled for 8 hours under reflux. After concentration under reduced pressure the residue is dissolved in 500 ml of toluene, washed twice with 200 ml 2 N hydrochloric acid, washed again with water and concentrated under reduced pressure. The residue comprising 296 g 2-carbethoxy-5-hydroxy-2'-methoxy-2,9,9-trimethyl-6,7-benzomorphan is dissolved in 5 l n-butanol and boiled under reflux under a nitrogen atmosphere with stirring for 18 hours with 665 g of calcium hydroxide. After cooling, 2 l of water are added, the organic and aequeous phases separated and the organic phase concentrated under reduced pressure. After conversion of the obtained residue into the hydrochloride and crystallization from methanol/ethylacetate 241.3 g of the title compound are obtained, m.p.: 217°–220° C. (with decomposition).

The following compounds of formula I wherein $R_1$ is hydrogen and $R_2$ is methyl are obtained in accordance with the above described processes 11a and 11b:

| No. 11 | Starting material | Method | Salt | m.p. (°C.) | $R_4$ | $R_3$ obtained product |
|---|---|---|---|---|---|---|
| c | 8a | 11b | HCl | 220–222(d) | $OCH_3$ | $CH_3$ |
| d | 1 | 11a | HCl | 217–220(d) | $OCH_3$ | H |
| e | 8c | 11a | Base | Oil | $OC_2H_5$ | $C_2H_5$ |
| f | 8e | 11b | HCl | 146–148 | $OCH_3$ | $C_2H_5$ |
| g | 8f | 11a | HCl | 203–205 | $OCH_3$ | allyl |
| h | 9b | 11a | Base | Oil | $OCH_3$ | $C_3H_7(n)$ |
| i | 8g | 11b | Base | Oil | $OCH_3$ | 2-butenyl |
| j | 9c | 11b | Base | Oil | $OCH_3$ | $C_4H_9(n)$ |
| k | 8h | 11b | Base | Oil | $OCH_3$ | benzyl |

EXAMPLE 12

9,9-dimethyl-2'-hydroxy-5-methoxy-6,7-benzomorphan hydrochloride

A solution of 40.0 g (120 mMol) 2-carbethoxy-2',5-dimethoxy-9,9-dimethyl-6,7-benzomorphan (intermediate of example 11c) in 20 ml diethylene-glycol are added drop-wise to a solution of 100 g potassium hydroxide in 480 ml ethylene-glycol previously heated to a temperature of 220° C. After heating for 8 hours at 210°–220° C. and subsequent cooling, 390 ml 4 N hydrochloric acid are added. After dilution with 1000 ml of ice-water, the reaction mixture is rendered basic by the addition of 150 ml 25% ammonia. The product is extracted 3 times with 250 ml chloroform/butanol (8:2) and the organic phase concentrated under reduced pressure. After conversion of the residue into the hydrochloride and crystallization from isopropanol/acetone (1:9) 13.4 g of the title compound are obtained, m.p.: 243°–246° C. (with decomposition).

EXAMPLE 13

9,9-dimethyl-2'-hydroxy-5-methoxy-6,7-benzomorphan hydrochloride

Method A

A solution of 285 ml ethanethiol (3,86 Mol) in 570 ml dimethylformamide (DMF) are added drop-wise to a suspension of 124.4 g (2.85 Mol) of sodium hydride (55% suspension in oil) in 1900 ml dry DMF. The obtained suspension is stirred for a further 45 minutes and a solution of 49.6 g (190 mMol) of 2',5-dimethoxy-9,9-dimethyl-6,7-benzomorphan (c.f. example 11a) in 190 ml of dry DMF are added drop-wise over 20 minutes. The initially formed volatile components are distilled off and the reaction mixture heated until the DMF boils. After boiling for 6 hours under reflux the reaction mixture is concentrated under reduced pressure and the residue taken up in 500 ml toluene and 2000 ml 2 N hydrochloric acid. The acid aequeous phase is made alkaline with 500 ml 25% ammonia and extracted 3 times with 500 ml chloroform/butanol (8:2). After evaporation of the organic phase, the residue is converted into the hydrochloride and crystallized from isopropanol to yield 29.0 g of the title compound (a) m.p.: 249°–251° C. (with decomposition).

Method B

A solution of 40 ml (352 mMol) of borontribromide in 250 ml dichloromethane are added drop-wise over a period of 45 minutes at room-temperature to a suspension of 59.5 g (200 mMol) of 2',5-dimethoxy-9,9-dimethyl-6,7-benzomorphan hydrochloride (c.f. example 11a) in 1000 ml dry dichloromethane. After stirring for 3 hours at room-temperature the reaction mixture is poured into 500 ml of ether. After the addition of 1 liter of water the mixture is rendered alkaline by the addition of approximately 150 ml 25% ammonia and extracted 5 times with chloroform/butanol (8:2). The combined organic phases are concentrated under reduced pressure, the residue converted into the hydrochloride and crystallized from methanol/ethylacetate to yield 48.8 g of the same title compound as previously, m.p.: 249°–252° C. (with decomposition).

Method C 11.4 g (38.3 mMol) of 2',5-dimethoxy-9,9-dimethyl-6,7-benzomorphan hydrochloride (c.f. example 11a) are added portionwise to a mixture of 14.4 g (115.3 mMol) aluminiumtrichloride, 14.5 ml of nitrobenzene and 250 ml of benzene. After boiling for 8 hours under reflux and cooling to 10° C. the obtained aluminiumtrichloride complex is extracted with 250 ml ice-cold 2 N hydrochloric acid, the temperature being kept below 40° C. After stirring for 30 minutes the acid aequeous phase is separated and rendered alkaline by addition of 25% ammonia. On standing a precipitate is formed, which is filtered off and washed with chloroform/butanol (8:2). The filtrate is extracted 3 times with chloroform/butanol (8:2) and concentrated under reduced pressure. The residue is chromatographed using 300 g basic aluminium oxide and chloroform/methanol (19:1) as eluent. The fractions containing the desired product are concentrated under reduced pressure, the residue converted into the hydrochloride and crystallized from methanol/ethylacetate to yield 2.7 g of the title compound, m.p.: 246°–249° C. (with decomposition).

The following compounds of formula I in which $R_2$ is methyl and $R_4$ is hydroxy are obtained analagously to processes A and B above (in the case of compound k, the 2'-methoxy group of the initially obtained product is removed by treatment with 47% hydrobromic acid analagously to example 7-method D):

| No. | Starting material | $R_1$ | $R_3$ obtained product | Method | Salt | m.p. (°C.) |
|---|---|---|---|---|---|---|
| b | 8b | $CH_3$ | $CH_3$ | B | Base | 183–185 |
| c | 8c | $CH_3$ | $C_2H_5$ | B | Oxalate | 216–218 |
| d | 9a | $CH_3$ | $n$-$C_3H_7$ | B | HCl | 243–246 |
| e | 8f | $CH_3$ | allyl | A | HCl | 227–232(d) |
| f | 10a | $CH_3$ | 3-hydroxy-propyl | A | HCl | 170(d) |
| g | 8g | $CH_3$ | 2-butenyl | A | HCl | 238–241 |
| h | 9c | $CH_3$ | $n$-$C_4H_9$ | A | HCl | 255–257 |
| i | 10b | $CH_3$ | 2-hydroxy-butyl | A | HCl | 243–246 |
| j | 8h | $CH_3$ | benzyl | A | HCl | 237–240 |
| k | 11b | H | H | D | HBr | 280–283(d) |
| l | 11f | H | $C_2H_5$ | B | Base | 208–210 |
| m | 11g | H | allyl | A | Base | 228–230 |
| n | 11h | H | $n$-$C_3H_7$ | A | HCl | 232–236 |
| o | 11i | H | 2-butenyl | A | Base | Oil |
| p | 11j | H | $n$-$C_4H_9$ | B | Base | Oil |
| q | 11k | H | benzyl | A | Base | Oil |

EXAMPLE 14

(a)
2-cyclobutylmethyl-2',5-dihydroxy-9,9-dimethyl-6,7-benzomorphan hydrochloride A solution of 3 g (25 mMol) cyclobutyl-carbonyl-chloride in 15 ml dichloromethane are added drop-wise in 10 minutes to a solution of 2.33 g (10 mMol) 2',5-dihydroxy-9,9-dimethyl-6,7-benzomorphan in 70 ml dichloromethane and 8 ml triethylamine. After boiling for 4 hours under reflux the reaction mixture is allowed to cool and is washed 3 times with 25 ml water and once with 25 ml 1 N hydrochloric acid. The organic phase is concentrated under reduced pressure and the residue dissolved in 20 ml dry tetrahydrofuran. The solution is added drop-wise to a suspension of 1.5 g (44.1 mMol) lithium-aluminium hydride in 25 ml tetrahydrofuran. After boiling under reflux for 5 hours and cooling, 7.5 g of sodium sulphate are added carefully. The obtained precipitate is filtered off, washed with tetrahydrofuran and the filtrate concentrated under reduced pressure. Conversion of the residue into its hydrochloride and crystallization from methanol/ethylacetate yields 2.5 g of the title compound, m.p.: 260°–262° C.

The following compounds are obtained analagously using the appropriate carboxylic acid chlorides (the substituents $R_2$, $R_3$ and $R_4$ in the product compounds are the same as in the starting materials):

| No. | Starting material | N—Substituent ($R_1$) | Salt | m.p. (°C.) |
|---|---|---|---|---|
| b | A | $CH_2CH_2OCH_2CH_3$ | HCl | 245–250 |
| c | A | $CH_2CH(OCH_3)CH_3$ | HCl | 235–238 |
| d | A | $CH_2C(CH_3)_2OCH_3$ | HCl | 234–238 |
| e | B |  $CH_2$— | Base | Oil |
| f | C | $CH_2CH_2CH_3$ | HCl | 220–222 |
| g | C | $CH_2CH_2CH_2CH_3$ | HCl | 212–214 |
| h | C |  $CH_2$— | HCl | 238–240 |
| i | C | $CH_2CH(OCH_3)CH_3$ | HCl | 219–224* |
| j | C | $CH_2CH_2C_6H_5$ | HCl | 224–229 |
| k | C |  $CH_2$— | HCl | 197–200 |
| l | C |  $CH_3$—, $CH_2$— | Oxalate | 188–190 |
| m | D |  $CH_2$— | HCl | 229–231 |
| n | D | $CH_2CH(OCH_3)CH_3$ | HCl | 210–213 |
| o | D | $CH_2CH_2OCH_2CH_3$ | HCl | 214–216 |
| p | D | $CH_2CH_2OCH(CH_3)_2$ | HCl | 198–202 |
| q | D | $CH_2CH(OCH_3)CH_2CH_3$ | HCl | 210–213 |
| r | E |  $CH_2$— | Base | Oil |
| s | F | $CH_2CH(OCH_3)CH_3$ | HCl | 214–216 |
| t | G | $CH_2CH(OCH_3)CH_3$ | HCl | 219–222 |
| u | H | $CH_2CH_2OCH_3$ | HCl | 164–167 |

*The diasterioisomeric mixture is separated by fractional crystallisation. M.p. of isomer X (HCl-salt) = 226–227° C., m.p. of isomer Y (methanesulfonic acid-salt) = 183–186° C.

| Starting materials | Example |
|---|---|
| A: 2',5-dihydroxy-9,9-dimethyl-6,7-benzomorphan | (8 k) |
| B: 2',5-dimethoxy-9,9-dimethyl-6,7-benzomorphan | (11 c) |
| C: 9,9-dimethyl-2'-hydroxy-5-methoxy-6,7-benzomorphan | (13 a) |
| D: 9,9-dimethyl-5-ethoxy-2'-hydroxy-6,7-benzomorphan | (13 l) |

-continued

| | | |
|---|---|---|
| E: | 5-allyloxy-9,9-dimethyl-2'-methoxy-6,7-benzomorphan | (11 g) |
| F: | 5-allyloxy-9,9-dimethyl-2'-hydroxy-6,7-benzomorphan | (13 m) |
| G: | 9,9-dimethyl-2'-hydroxy-5-propoxy-6,7-benzomorphan | (13 n) |
| H: | 5-butyloxy-9,9-dimethyl-2'-hydroxy-6,7-benzomorphan | (13 p) |

EXAMPLE 15

(a) 2-allyl-9,9-dimethyl-2'-hydroxy-5-methoxy-6,7-benzomorphan hydrochloride

A mixture of 1.4 g (5 mMol) 9,9-dimethyl-2'-hydroxy-5-methoxy-6,7-benzomorphan hydrochloride, 1.04 g (7,5 mMol) calcium carbonate and 0.75 g (6.25 mMol) of allylbromide in 25 ml dimethylformamide is heated to 70° C. for 3½ hours and subsequently concentrated under reduced pressure. The residue is taken up in a mixture of 50 ml water and 50 ml chloroform and the aequeous phase extracted twice with chloroform-/butanol (9:1). The combined organic phases are concentrated under reduced pressure. The residue is converted into the hydrochloride and crystallized from methanol/ethylacetate to yield 1.38 g of the title compound, m.p.: 218°–220° C. (with decomposition).

The following compounds are obtained analagously by alkylation of the indicated starting material with a compound RX:

| No. | Starting material | N—Substituent (—R of RX) | X of RX | Salt | m.p. (°C.) |
|---|---|---|---|---|---|
| b | A | CH₂CH₂C≡CH | OSO₂C₆H₅CH₃ | HCl | 235–237 |
| c | B | CH₂CH=C(CH₃)₂ | Br | Oxalate | 196–198 |
| d | C | CH₂C≡CH | Br | HCl | 216–218 |
| d' | C | CH₂CH₂C≡CH | OSO₂C₆H₅CH₃ | HCl | 193–197 |
| e | C | CH₂—⟨tetrahydrofuran⟩ | Br | HCl | 201–203 |
| f | C | CH₂C(O)CH₃ | Br | Base | Oil |
| g | D | CH₂CH=C(CH₃)₂ | Br | HCl | 204–206 |
| h | D | CH₂—⟨tetrahydrofuran⟩ | Br | HCl | 230–234 |
| i | D | CH₂COOC₂H₅ | Br | Base | Oil |

The compound i is employed for further reaction directly without purification.

Starting materials A, B, C, D are as shown in example 14.

EXAMPLE 16

(a) 2',5-dihydroxy-9,9-dimethyl-2-(2-hydroxy-2-methylpropyl)-6,7-benzomorphan hydrochloride A mixture of 20.0 g (85.8 mMol) of 2',5-dihydroxy-9,9-dimethyl-6,7-benzomorphan (A) and 15.3 ml (172 mMol) of 1,2-epoxy-2-methylpropan in 150 ml methanol is heated in an autoclave for 5 hours at 100° C. After cooling the solution is concentrated at reduced pressure and the residue filtered over 300 g silicagel using ethylacetate as eluent. Fractions containing the desired product are combined and concentrated under reduced pressure. The residue is converted into the hydrochloride and crystallized from methanol/ethylacetate to yield 23.3 g of the title compound, m.p.: 235°–239° C. (with decomposition).

The following compounds in which the substituents R₂, R₃ and R₄ and the same as in starting materials may be produced analagously:

| No. | Starting material | N—Substituent of product compound | Salt | m.p. (°C.) |
|---|---|---|---|---|
| b | A | CH₂—⟨cyclopropyl⟩, OH | HCl | 241–248 |
| c | A | CH₂—⟨cyclobutyl⟩, OH | HCl | 245 (d) |
| d | A | CH₂—⟨cyclopentyl⟩, OH | HCl | 227–230 |
| e | B | CH₂—⟨cyclopropyl⟩, OH | HCl | 201–206 |
| f | C | CH₂C(OH)(CH₃)₂ | HCl | 207–210 |
| g | C | CH₂CH(OH)C₆H₅ | Base | 170–175 |
| h | C | CH₂—⟨cyclopropyl⟩, OH | HCl | 160–169 |
| i | C | CH₂—⟨cyclobutyl⟩, OH | HCl | 231–234 |
| j | C | CH₂—⟨cyclopentyl⟩, OH | HCl | 218–221 |
| k | D | CH₂C(OH)(CH₃)₂ | HCl | 197–200 |
| l | D | CH₂—⟨cyclopropyl⟩, OH | HCl | 225–229 |
| m | D | CH₂—⟨cyclobutyl⟩, OH | HCl | 228–234 |
| n | D | CH₂CH(OH)CH₂OCH₃ | Base | Oil |
| o | F | CH₂C(OH)C(CH₃)₂ | HCl | 201–203 |
| p | G | CH₂C(OH)(CH₃)₂ | HCl | 208–212 |
| q | H | CH₂—⟨cyclopropyl⟩, OH | HCl | 209–212 |
| r | I | CH₂C(OH)(CH₃)₂ | HCl | 193–195 |
| s | I | CH₂—⟨cyclopropyl⟩, OH | HCl | 188–191 |
| t | J | CH₂C(OH)(CH₃)₂ | HCl | 203–205 |
| u | J | CH₂—⟨cyclopropyl⟩, OH | HCl | 203–205 |
| v | A | CH₂C(OH)CH₂OCH₃*(A) | Base | Oil** |

-continued

| No. | Starting material | N—Substituent of product compound | Salt | m.p. (°C.) |
|---|---|---|---|---|
| w | A | CH₂C(OH)CH₂OCH₃*(B) | Base | 148–151° C. |

*The diastereomers A and B are separated using thin layer chromatography.
**The raw product is used directly for further reaction in accordance with example 19.

Starting materials

The starting materials A to H are the same as those given in example 14. Starting material I is 5-(2-butenyloxy)-9,9-dimethyl-2'-hydroxy-6,7-benzomorphan (compound of example 13o). The starting material J is 5-benzyloxy-9,9-dimethyl-2'-hydroxy-6,7-benzomorphan (the compound of example 13q).

EXAMPLE 17

(a) Starting from 2-cyclobutylmethyl-2',5-dimethoxy-9,9-dimethyl-6,7-benzomorphan (example 14e) and proceeding analagously to example 13, method A there is obtained 2-cyclobutylmethyl-9,9-dimethyl-2'-hydroxy-5-methoxy-6,7-benzomorphan hydrochloride, m.p.: 225°–227° C.

(b) Starting from 2',5-dimethoxy-9,9-dimethyl-2-(3-methyl-2-butenyl)-6,7-benzomorphan hydrochloride (example 15c) and proceeding according to the method of example 13, method B there is obtained 9,9-dimethyl-2'-hydroxy-2-(3-methyl-2-butenyl)-5-methoxy-6,7-benzomorphan oxalate, m.p.: 206°–207° C. (with decomposition).

(c) Starting from 5-allyloxy-2-cyclobutylmethyl-9,9-dimethyl-2'-methoxy-6,7-benzomorphan (example 14r) and proceeding in accordance with the method of example 13, method A there is obtained 5-allyloxy-2-cyclobutylmethyl-9,9-dimethyl-2'-hydroxy-6,7-benzomorphan hydrochloride, m.p.: 223°–228° C.

EXAMPLE 18

2-cyclobutylmethyl-9,9-dimethyl-2'-hydroxy-5-propoxy-6,7-benzomorphan hydrochloride Starting from 5-allyloxy-2-cyclobutylmethyl-9,9-dimethyl-2'-hydroxy-6,7-benzomorphan hydrochloride (example 17c) and proceeding in accordance with the method of example 9a, the title compound is obtained, m.p.: 221°–225° C.

EXAMPLE 19

Proceeding in accordance with the method of example 8b and example 13, method A the following compounds of formula I are obtained:

| No. | Starting material | N—Substituent of product compound | Salt | m.p. (°C.) |
|---|---|---|---|---|
| a | 16 f | CH₂C(OCH₃)(CH₃)₂ | HCl | 180–185 |
| b | 16 k | CH₂C(OCH₃)(CH₃)₂ | HCl | 184–188 |
| c | 16 n | CH₂CH(OCH₃)CH₂OCH₃ | HCl | 188–192 |
| d | 16 l | CH₃O<br>CH₂— | HCl | 226–230 |
| e | 16 m | CH₃O<br>CH₂— | HCl | 211–220 |
| f* | 16 b | CH₃O<br>CH₂— | HCl | 239–251 |
| g | 16 v | CH₂CH(OCH₃)CH₂OCH₃** | HCl | 190–193 |

*N.B.: In the process of example 19 f the amounts of sodium-hydride and methyliodide are reduced to two equivalents, in order that the 5-hydroxy group remains intact.
**Isomer A.

EXAMPLE 20

(a) 2'-hydroxy-5-propionyloxy-2,9,9-trimethyl-6,7-benzomorphan hydrochloride 3.0 g (12 mMol) of 2',5-dihydroxy-2,9,9-trimethyl-6,7-benzomorphan hydrochloride (c.f. example 2) are heated for 3 hours in a mixture of 45 ml propionic acid anhydride and 6 g othophosphoric acid. After cooling the reaction mixture is poured into 100 g of ice-water and adjusted to pH8 by addition of dilute sodium hydroxide. The aequeous phase is extracted 3 times with 25 ml chloroform, the combined chloroform extracts dried over magnesium sulphate and concentrated at reduced pressure. The residue is dissolved in dry ether and carefully acidified by the addition of isopropanol/HCl. The obtained precipitate is filtered off and washed with ether to yield 3.6 g of 2',5-dipropionyloxy-2,9,9-trimethyl-6,7-benzomorphan hydrochloride, m.p.: 213°–217° C.

3.6 g (9,1 mMol) of this di-ester are dissolved in 25 ml isopropanol, 5 ml 5 N isopropanol/HCl are added and the obtained solution boiled for 4 hours under reflux. The solvent is evaporated off under reduced pressure. The residue is treated with acetone and the obtained cyrstals filtered off to yield 2,8 g of the title compound, m.p.: 227°–230° C.

(b) Proceeding analagously, but using acetic acid anhydride in place of propionic acid anhydride and without isolation of the intermediate there is obtained 5-acetoxy-2'-hydroxy-2,9,9-trimethyl-6,7-benzomorphan, m.p.: 158°–160° C.

(c) Starting from 2',5-dihydroxy-9,9-dimethyl-6,7-benzomorphan (c.f. example 13k) and proceeding analagously to example 13b there is obtained 2',5-diacetoxy-9,9-dimethyl-6,7-benzomorphan. This is used for further reaction without purification.

(d) Starting from 9,9-dimethyl-2'-hydroxy-2-(2-hydroxy-2-methylpropyl)-5-methoxy-6,7-benzomorphan hydrochloride (c.f. example 16f) and proceeding analagously to example 20a there is obtained 9,9-dimethyl-5-methoxy-2'-propionyloxy-2-(2-methyl-2-propionyloxypropyl)-6,7-benzomorphan hydrochloride, m.p.: 96°–102° C.

After hydrolysis of the 2'-propionyloxy group there is obtained 9,9-dimethyl-2'-hydroxy-5-methoxy-2-(2-methyl-2-propionyloxypropyl)-6,7-benzomorphan, m.p.: 178°–180° C.

(e) Starting from 5-ethoxy-9,9-dimethyl-2'-hydroxy-2-(2-hydroxy-2-methylpropyl)-6,7-benzomorphan hydrochloride (c.f. example 16k) and proceeding analagously to example 20a there is obtained 9,9-dimethyl-5-ethoxy-2'-hydroxy-2-(2-methyl-2-propionyloxypropyl)-6,7-benzomorphan, m.p.: 160°–163° C.

EXAMPLE 21

(a) 5-hydroxy-2,9,9-trimethyl-6,7-benzomorphan hydrochloride

A mixture of 3.7 g (15 mMol) of 2',5-dihydroxy-2,9,9-trimethyl-6,7-benzomorphan (c.f. example 2), 3 g (16.5 mMol) of 5-chloro-1-phenyl-tetrazole and 5 g calcium carbonate in 100 ml dry dimethylformamide is heated at 100° C. for 5 hours. After cooling the salt is filtered off and the filtrate concentrated at reduced pressure. The residue is extracted with 25 ml acetone and 25 ml ether. The obtained crystals are filtered off and dried to yield 3.3 g of 2'-(1-phenyl-5-tetrazolyloxy-5-hydroxy-2,9,9-trimethyl-6,7,benzomorphan, m.p.: 158°–164° C.

3.12 g (8 mMol) of this product dissolved in 250 ml ethanol are hydrogenated using 500 ml palladium on active charcoal (5%) as catalyst. After uptake of the theoretical amount of hydrogen the catalyst is filtered off and the solvent concentrated under reduced pressure. The residue is taken up in 25 ml toluene and extracted twice with 25 ml 1 N hydrochloric acid. The acid aequeous phase is rendered alkaline with 25% ammonia and extracted twice with 25 ml chloroform. The organic phase is dried over magnesium sulphate and concentrated under reduced pressure. The residue is converted to the hydrochloride and crystallized from acetone to yield 1.0 g of the title compound, m.p.: 250°–252° C.

(b) Starting from 2'-hydroxy-5-methoxy-2,9,9-trimethyl-6,7-benzomorphan (c.f. example 13b) and proceeding analagously there is obtained 5-methoxy-2,9,9-trimethyl-6,7-benzomorphan hydrochloride, m.p.: 218°–223° C.

(c) Starting from 9,9-dimethyl-5-ethoxy-2'-hydroxy-6,7-benzomorphan (c.f. example 13l) and proceeding analagously there is obtained 9,9-dimethyl-5-ethoxy-6,7-benzomorphan as a non-crystalline material.

EXAMPLE 22

5-acetoxy-2,9,9-trimethyl-6,7-benzomorphan hydrochloride

Starting from 5-hydroxy-2,9,9-trimethyl-6,7-benzomorphan hydrochloride (c.f. example 21a) and proceeding according to example 20b) the title compound is obtained, m.p.: 225°–227° C.

EXAMPLE 23

9,9-dimethyl-5-methoxy-6,7-benzomorphan

Starting from 5-methoxy-2,9,9-trimethyl-6,7-benzomorphan (c.f. example 21b) and proceeding according to the method of example 11b, the title compound is obtained. This is used for further reaction without purification.

EXAMPLE 24

9,9-dimethyl-2-(1-hydroxycyclopropyl-methyl)-5-methoxy-6,7-benzomorphan hydrochloride Starting from 9,9-dimethyl-5-methoxy-6,7-benzomorphan (c.f. example 23) and proceeding in accordance with the method of example 16 and using oxaspiropentane as the epoxide the title compound is obtained, m.p.: 193°–195° C.

EXAMPLE 25

5-acetoxy-9,9-dimethyl-2'-hydroxy-2-(2-hydroxy-2-methylpropyl)-6,7-benzomorphan hydrochloride Starting from 2',5-diacetoxy-9,9-dimethyl-6,7-benzomorphan (c.f. example 20c) and proceeding in accordance with the method of example 16 using 1,2-epoxy-2-methylpropan and with subsequent cleavage of the 2'-acetoxy group in accordance with the method of example 20a the title compound is obtained, m.p.: 201°–203° C.

EXAMPLE 26

9,9-dimethyl-2'-hydroxy-2-(2-hydroxy-2-methylpropyl)-5-propionyloxy-6,7-benzomorphan hydrochloride Starting from 2',5-dihydroxy-9,9-dimethyl-6,7-benzomorphan (c.f. example 13k) and proceeding in accordance with the method of example 15, using 2 equivalents of benzylbromide, 2-benzyl-2'-benzyloxy-9,9-dimethyl-5-hydroxy-6,7-benzomorphan is obtained. This compound is reacted with propionic acid anhydride in accordance with the method of example 20 to produce 2-benzyl-2'-benzyloxy-9,9-dimethyl-5-propionyloxy-6,7-benzomorphan. After hydrogenolysis of the benzyl groups there is obtained 9,9-dimethyl-2'-hydroxy-5-propionyloxy-6,7-benzomorphan. This compound is then reacted with 1,2-epoxy-2-methylpropan in accordance with the method of example 16 to obtain the title compound, m.p.: 197°–198° C.

EXAMPLE 27

(a) 2'-acetoxy-5-hydroxy-2-(1-acetoxy-cyclopropylmethyl)-9,9-dimethyl-6,7-benzomorphan 60 g (19.8 mMol) of 2',5-dihydroxy-2-(1-hydroxycyclopropylmethyl)-9,9-dimethyl-6,7-benzomorphan (c.f. example 16b) are refluxed for 1 hour in 60 ml acetic anhydride together with a few drops of pyridine. The solution is evaporated to dryness, the residue dissolved in water, the aequeous solution rendered basic with ammonium hydroxide and extracted with ethyl acetate. The combined organic phases are washed with water, dried and evaporated under reduced pressure. The residue is chromatographed over SiO₂ with toluene/ethyl acetate (1:1) as eluant to yield the title compound as an oil.

(b) 2',5-dihydroxy-2-(1-acetoxy-cyclopropylmethyl)-9,9-dimethyl-6,7-benzomorphan oxalate The diacetate obtained under (a) above is dissolved in 50 ml methanol and rendered neutral with 1 N hydrochloric acid. A catalytic amount (19 mg) of p-toluenesulphonic acid is added and the solution refluxed for 1½ hours. The solution is evaporated to dryness under reduced pressure, and the residue dissolved in water. After carefully rendering basic with concentrated ammonium hydroxide, the solution is extracted with ethylacetate, the collected organic phases washed with water, dried over magnesium sulphate and evaporated under reduced pressure. The base obtained after chromatography over SiO₂ with toluene/ethylacetate (1:1) as eluant is converted into the oxalate and the product recrystallised from methanol/ethylacetate to yield the title compound, m.p. 196°–198° C.

EXAMPLE 28

9,9-dimethyl-5-ethoxy-2'-hydroxy-2-(2-hydroxy-2-methylpropyl)-6,7-benzomorphan hydrochloride A solution of 2,77 g (8 mMol) of 9,9-dimethyl-5-ethoxy-2-carbethoxymethyl-2'-hydroxy-6,7-benzomorphan (c.f. example 15i) in 100 ml ether is added dropwise to 100 mMol methylmagnesium iodide in 100 ml ether. The mixture is boiled for 1 hour under reflux and cooled. The excess magnesium compound is decomposed by the addition of dilute hydrochloric acid, the acid aqueous phase rendered alkali with 25% ammonia and extracted 3 times with 50 ml of chloroform. The combined organic phases are evaporated to dryness under reduced pressure. The residue is converted into the hydrochloride and crystallized from methanol-/ethylacetate to yield 1.29 g of the title compound, m.p.: 208°–211° C.

EXAMPLE 29

(+) and (−)-5-hydroxy-2′-methoxy-2,9,9-trimethyl-6,7-benzomorphan hydrochloride

A solution of 13.0 g (50 mMol) (±)-5-hydroxy-2′-methoxy-2,9,9-trimethyl-6,7-benzomorphan in 125 ml ethanol is added to a solution of 11.6 g (50 mMol) of d-camphorsulphonic acid in 125 ml water. The mixture is evaporated to dryness under reduced pressure. 125 ml methanol, 250 ml ethylacetate and 250 ml ether are added to the residue, to yield 6.0 g of the crystalline (++)-salt. The salt is crystallized twice from methanol-/ethylacetate, until a constant melting point of 225°–229° C. and a constant rotation of $[\alpha_D]_{25} = +76°$ is obtained. Yield 4.2 g. A further 3 g are obtained from the mother-liquor after slight evaporation. Further evaporation of the mother-liquor yields the (−+)-salt, which after double recrystallization has the melting point of 218°–222° C. and a rotation of $[\alpha]_D^{25} = -36°$. The (+)-base is obtained from the (++)-salt by treatment with concentrated ammonia and is converted into the hydrochloride, m.p.: 248°–252° C. and $[\alpha]_D^{25} = +90.5°$. The (−+)-salt is similarly treated with concentrated ammonia and the obtained (−)-base converted to the hydrochloride, m.p.: 250°–253° C., $[\alpha]_D^{25} = -91°$ C.

EXAMPLE 30

(+)-2′-hydroxy-5-methoxy-2,9,9-trimethyl-6,7-benzomorphan hydrochloride

Starting from (+)-5-hydroxy-2′-methoxy-2,9,9-trimethyl-6,7-benzomorphan (c.f. example 28) and proceeding in accordance with the method of example 8a and example 13, method A the title compound is obtained, m.p.: 220°–223° C. and $[\alpha]_D^{25} = +84.7°$ C.

EXAMPLE 31

(−)-2′-hydroxy-5-methoxy-2,9,9-trimethyl-6,7-benzomorphan hydrochloride

Starting from (−)-5-hydroxy-2′-methoxy-2,9,9-trimethyl-6,7-benzomorphan (c.f. example 28) and proceeding analagously to example 29 the title compound is obtained, m.p.: 219°–222° C. and $[\alpha]_D^{25} = -83.1°$.

We claim:
1. A method of inhibiting luteinising hormone secretion in a subject in need of such treatment, which method comprises administering to said subject a luteinising hormone secretion inhibiting effective amount of a compound of formula I

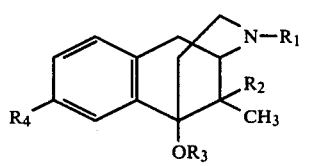

(I)

wherein
$R_1$ is hydrogen; alkyl, alkenyl, alkynyl, cycloalkyl or cycloalkylalkyl, each of which may be substituted with either hydroxy or alkoxy or with both; alkenyloxyalkyl, aralkyl, arylhydroxyalkyl, aralkenyl, tetrahydrofurylalkyl or optionally alkyl-substituted furylalkyl or isoxazolylalkyl,
$R_2$ is hydrogen or methyl,
$R_3$ is hydrogen, alkyl, alkenyl, alkynyl, aralkyl, hydroxyalkyl or alkoxyalkyl and
$R_4$ is hydrogen, hydroxy, alkoxy or alkenyloxy, whereby hydroxy groups in said compound may each be optionally acylated; or a pharmaceutically acceptable acid addition salt thereof.

2. A method according to claim 1 wherein, in the compound of formula I
$R_1$ is hydrogen, $C_{1-6}$ alkyl, $C_{1-6}$ hydroxyalkyl, $C_{2-6}$(alkoxy-alkyl) in which the alkyl moiety is optionally mono-substituted by hydroxy or methoxy, $C_{3-6}$ alkenyl, $C_{3-6}$ alkynyl, $C_{4-7}$(cycloalkylmethyl), $C_{4-7}$[(1-hydroxy-cycloalkyl)-methyl)], $C_{5-8}$[(1-methoxy-cycloalkyl)-methyl], $C_{7-10}$(phenylalkyl), $C_{7-10}$(phenylhydroxyalkyl), tetrahydrofurylmethyl or furylmethyl optionally ring-substituted by methyl,
$R_2$ is hydrogen or methyl,
$R_3$ is hydrogen, $C_{1-4}$ alkyl, $C_{1-4}$ hydroxyalkyl, $C_{3-4}$ alkenyl, $C_{3-4}$ alkynyl or $C_{7-9}$(phenylalkyl) and
$R_4$ is hydrogen, hydroxy, $C_{1-4}$ alkoxy or $C_{3-4}$ alkenyloxy,
whereby hydroxy groups in said compound may each be optionally acylated.

3. A method according to claim 2 wherein, in the compound of formula I
$R_1$ is (1-hydroxy-cyclobutyl)-methyl,
$R_2$ is methyl,
$R_3$ is hydrogen, and
$R_4$ is hydroxy.

4. A method according to claim 2 wherein in the compound of formula I
$R_1$ is (1-hydroxy-cyclopropyl)-methyl,
$R_2$ and $R_3$ are each methyl and
$R_4$ is hydroxy.

5. A method according to claim 1 wherein in the compound of formula I
$R_1$ is (1-hydroxy-cyclopropyl)-methyl,
$R_2$ is methyl,
$R_3$ is ethyl and
$R_4$ is hydroxy.

6. A method according to claim 1 wherein in the compound of formula I
$R_1$ is (1-methoxy-cyclopropyl)-methyl,
$R_2$ is methyl,
$R_3$ is hydrogen and
$R_4$ is hydroxy.

7. A method according to claim 1 for the treatment of menopausal syndrome.

8. A method according to claim 1 for the treatment of post-menopausal hot flashes.

9. A method according to claim 1 for the treatment of prostate hypertrophy.

10. A method according to claim 1 wherein the compound is administered at a daily dosage of from about 0.1 to about 20 mg.

11. A method according to claim 10 wherein the compound is administered at a daily dosage of from about 0.5 to about 4 mg.

12. A method according to claim 10 wherein the compound is administered orally and in unit dosage form.

13. The method according to claim 1, wherein $R_1$ is 2-hydroxy-2-methyl-n-propyl, $R_2$ is methyl, $R_3$ is hydrogen and $R_4$ is hydroxy in the compound of formula (I).

14. The method according to claim 1, wherein $R_1$ is (1-hydroxy-cyclopentyl)-methyl, $R_2$ is methyl, $R_3$ is hydrogen and $R_4$ is hydroxy in the compound of formula (I).

15. The method according to claim 1, wherein $R_1$ is 2-hydroxy-2-methyl-n-propyl, $R_2$ and $R_3$ are both methyl and $R_4$ is hydroxy in the compound of formula (I).

16. The method according to claim 1, wherein $R_1$ is (1-hydroxy-cyclopentyl)-methyl, $R_2$ and $R_3$ are both methyl and $R_4$ is hydroxy in the compound of formula (I).

17. The method according to claim 1, wherein $R_1$ is (1-hydroxy-cyclopropyl)-methyl, $R_2$ is methyl, $R_3$ is n-butyl and $R_4$ is hydroxy in the compound of formula (I).

* * * * *